US009939412B2

(12) United States Patent
Ichimura et al.

(10) Patent No.: US 9,939,412 B2
(45) Date of Patent: Apr. 10, 2018

(54) DEVICES, SYSTEMS, AND METHODS FOR DETECTING ODORANTS

(71) Applicant: EMPIRE TECHNOLOGY DEVELOPMENT LLC, Wilmington, DE (US)

(72) Inventors: Naoya Ichimura, Kyoto (JP); Tatsuaki Hirase, Nara (JP)

(73) Assignee: EMPIRE TECHNOLOGY DEVELOPMENT LLC, Wilmington, DE (US)

( * ) Notice: Subject to any disclaimer, the term of this patent is extended or adjusted under 35 U.S.C. 154(b) by 18 days.

(21) Appl. No.: 14/766,365

(22) PCT Filed: Feb. 6, 2013

(86) PCT No.: PCT/US2013/024887
§ 371 (c)(1),
(2) Date: Aug. 6, 2015

(87) PCT Pub. No.: WO2014/123519
PCT Pub. Date: Aug. 14, 2014

(65) Prior Publication Data
US 2015/0377835 A1 Dec. 31, 2015

(51) Int. Cl.
*G01N 29/02* (2006.01)
*G01N 29/036* (2006.01)
(Continued)

(52) U.S. Cl.
CPC ......... *G01N 29/036* (2013.01); *G01N 29/022* (2013.01); *G01N 29/4418* (2013.01);
(Continued)

(58) Field of Classification Search
CPC ............... G01N 29/022; G01N 29/036; G01N 29/2437; G01N 29/2443; G01N 29/245;
(Continued)

(56) References Cited

U.S. PATENT DOCUMENTS 3,325,733 A 6/1967 Lemelson
3,796,968 A 3/1974 Luscher
(Continued)

FOREIGN PATENT DOCUMENTS

JP H07190916 7/1995
JP H0943182 2/1997
(Continued)

OTHER PUBLICATIONS

Machine translation of JP Patent No. 3,139,562 to Yokoyama et al. published on Mar. 5, 2001.*
(Continued)

*Primary Examiner* — Blake A Tankersley
(74) *Attorney, Agent, or Firm* — Dorsey & Whitney LLP

(57) ABSTRACT

Devices, systems, and methods for sensing one or more odorants are disclosed. The device may include an oscillator crystal coated with a polymer. The oscillator crystal may typically oscillate at a known first frequency. The coated crystal may respond to exposure to an odorant by oscillating at one or more alternative frequencies. The coated crystal response may depend on the polymer composition, polymer concentration, coating geometry, and/or odorant to which it may be exposed. The system may include one or more oscillator crystals, each coated with a different polymer composition, polymer concentration, and/or coating geometry. The system may include non-coated crystals. The system may also include additional electronics to measure the frequencies of the one or more coated or non-coated crystals and to analyze their frequencies. The method may include the use of such devices and/or systems to identify and/or determine the concentration of one or more odorants.

27 Claims, 10 Drawing Sheets

110
130a
130b
120a
120b

(51) Int. Cl.
*G01N 29/44* (2006.01)
*G01N 33/00* (2006.01)

(52) U.S. Cl.
CPC ..... *G01N 29/4481* (2013.01); *G01N 33/0001* (2013.01); *G01N 2291/014* (2013.01); *G01N 2291/021* (2013.01); *G01N 2291/0256* (2013.01); *G01N 2291/0426* (2013.01)

(58) Field of Classification Search
CPC ............. G01N 2291/0426; G01N 5/02; G01N 33/54373
See application file for complete search history.

(56) References Cited

U.S. PATENT DOCUMENTS 4,188,557 A 2/1980 Mattuschka
4,375,604 A 3/1983 Vig
4,547,748 A 10/1985 Ballato
4,792,433 A 12/1988 Katsura et al.
5,049,808 A 9/1991 Okahata
5,493,922 A 2/1996 Ramey et al.
5,596,243 A 1/1997 Tsuru et al.
5,789,659 A 8/1998 Williams
6,068,746 A 5/2000 Kojima et al.
6,171,378 B1 1/2001 Manginell et al.
6,196,052 B1 * 3/2001 May ...................... B01D 53/30 73/24.06
6,222,366 B1 * 4/2001 Dilger ..................... G01G 3/13 324/300
6,238,085 B1 5/2001 Higashi et al.
6,432,362 B1 8/2002 Shinar et al.
6,457,361 B1 10/2002 Takeuchi et al.
6,495,105 B1 12/2002 Yamada et al.
6,510,738 B1 1/2003 Lee et al.
6,537,498 B1 3/2003 Lewis et al.
6,858,182 B1 2/2005 Ito et al.
6,862,917 B2 3/2005 Apostolos et al.
7,046,096 B2 5/2006 Kobayashi
7,055,377 B2 6/2006 Paul et al.
7,075,216 B1 7/2006 Vetelino
7,076,371 B2 7/2006 Fu
7,321,272 B2 1/2008 Neumann
7,591,200 B2 9/2009 Takahashi et al.
7,767,068 B2 8/2010 Lauks et al.
7,770,273 B2 8/2010 Abe et al.
7,846,489 B2 12/2010 Chang
7,993,506 B2 8/2011 Nakano et al.
8,739,604 B2 6/2014 Krishna et al.
2002/0023480 A1 2/2002 Hattori et al.
2002/0142478 A1 10/2002 Wado et al.
2003/0060726 A1 3/2003 Lin et al.
2003/0089623 A1 5/2003 Peat et al.
2003/0132811 A1 7/2003 Nagaura
2003/0137216 A1 7/2003 Tamayo de Miguel et al.
2004/0047239 A1 3/2004 Benjamin
2006/0058697 A1 3/2006 Mochizuki et al.
2006/0096370 A1 5/2006 Isogai et al.
2006/0257286 A1 11/2006 Adams
2007/0007851 A1 1/2007 Loebl et al.
2007/0117983 A1 5/2007 Dayagi et al.
2007/0144795 A1 6/2007 Tran
2007/0251321 A1 11/2007 Fritze et al.
2008/0229829 A1 9/2008 Kondo
2009/0151428 A1 6/2009 Bhethanabotla et al.
2009/0293590 A1 12/2009 Zeng et al.
2010/0060386 A1 3/2010 Belot et al.
2010/0112680 A1 5/2010 Brockwell et al.
2010/0151128 A1 6/2010 Koinuma et al.
2011/0008212 A1 1/2011 Ichimura
2011/0128003 A1 6/2011 Thompson et al.
2011/0266919 A1 11/2011 Ikehara et al.
2011/0269632 A1 11/2011 Haick et al.
2011/0283801 A1 11/2011 Matsumoto
2012/0090389 A1 4/2012 Aastrup
2012/0103066 A1 5/2012 Xia et al.
2012/0103099 A1 5/2012 Stuke et al.
2012/0112099 A1 5/2012 Coleman et al.
2015/0160145 A1 6/2015 Feyh et al.
2016/0077057 A1 3/2016 Fujii
2016/0146761 A1 5/2016 Fujii

FOREIGN PATENT DOCUMENTS

JP H10142134 A 5/1998
JP H10170422 A 6/1998
JP 2000341375 A 12/2000
JP 3139562 B2 3/2001
JP 2003090812 3/2003
JP 2003307481 A 10/2003
JP 2004184124 7/2004
JP 2004312286 A 11/2004
JP 2005017148 A 1/2005
JP 2006075447 A 3/2006
JP 2006275862 A 10/2006
JP 2007158419 A 6/2007
JP 2007167264 7/2007
JP 2007205993 8/2007
JP 2007205993 A 8/2007
JP 2007205994 A 8/2007
JP 2007212258 A 8/2007
JP 2007251826 9/2007
JP 2008110099 A 5/2008
JP 2008215993 A 9/2008
JP 2009236607 A 10/2009
JP 2010127625 6/2010
JP 2011189314 9/2011

OTHER PUBLICATIONS

Abe et al., A Monolithic QCM Array Designed for Mounting on a Flow Cell, IEEE Sensors Journal, vol. 11, Issue 1, pp. 86-90 (Jun. 10, 2010).
Cao et al., A perfume odour-sensing system using an array of piezoelectric crystal sensors with plasticized PVC coatings, Fresenius Journal of Analytical Chemistry, vol. 355, No. 2, pp. 194-199 (May 1996).
International Search Report and Written Opinion for International Application No. PCT/US2013/024949 dated Apr. 29, 2013.
Jaruwongrungsee et al., Analysis of Quartz Crystal Microbalance Sensor Array with Circular Flow Chamber, International Journal of Applied Biomedical Engineering, vol. 2, No. 2, pp. 50-54 (2009).
Ping et al., A novel method for diabetes diagnosis based on electronic noses, Biosensors and Bioelectronics, vol. 12, No. 9-10, pp. 1031-1036 (Nov. 1997).
Strashilov et al., Polymer-Coated Quartz Microbalance Sensors for Volatile Organic Compound Gases, Sensor Letters, vol. 7, No. 2, pp. 203-211 (Apr. 2009).
Tuantranont et al., A review of monolithic multichannel quartz crystal microbalance: A review, Analytica Chimica Acta, vol. 687, Issue 2, pp. 114-128 (Feb. 21, 2011).
Watsuji, The Current State of Digital Healthcare, New Business Development Division, Medical and Healthcare Business Development Center, pp. 7-11 (Jul. 2013).
Xu et al., Electrical Properties of Tungsten Trioxide Films, Journal of Vacuum Science and Technology, vol. 8, Issue 4, pp. 3634-3638 (1990).
International Search Report for International Application No. PCT/US2013/024887 dated Apr. 4, 2013.
Kim et al., Fabrication and application of an activated carbon-coated quartz crystal sensor, *Sensors and Actuators B* (2002), 87:196-200.
"International Search Report and Written Opinion for International Application No. PCT/US2014/013871, dated May 14, 2014".
"International Search Report and Written Opinion for International Application No. PCT/US2014/013877, dated May 12, 2014".
"International Search Report and Written Opinion for International Application No. PCT/US2013/036812 dated Aug. 2, 2013".

(56) References Cited

OTHER PUBLICATIONS

"International Search Report and Written Opinion of International Application No. PCT/US2013/046146 dated Dec. 2, 2013".
Abe, Takashi et al., "A Monolithic QCM Array Designed for Mounting on a Flow Cell", IEEE Sensors Journal. vol. 11, No. 1, Jan. 2011, 86-90.
Frietsch, M. et al., "Wedge-shaped ceramic membranes for gas sensor applications produced by a variety of CVD techniques", Surface and Coatings Technology 120-121, 1999, 265-271.
Goschnick, J. , "An electronic nose for intelligent consumer products based on a gas analytical gradient microarray", Microelectronic Engineering 57-58, 2001, 693-704.
Li, et al., "High Sensitive, Miniaturized Plano-Convex Quartz Crystal Microbalance Fabricated by Reactive Ion Etching and Melting Photoresist", The 12th International Conference on Transducers, Solid State Sensors, Actuators and Microsystems, vol. 1, Jun. 8-12, 2003, pp. 508-511.
Tuantranont, Adisorn et al., "A review of monolithic multichannel quartz crystal micro balance: A review", Analytica Chimica Acta, vol. 687, Feb. 21, 2011, 114-128.
Vashist, Sandeep K. et al., "Recent Advances in Quartz CrystalMicrobalance-Based Sensors", Journal of Sensors, vol. 2011, Article ID 571405, Jun. 30, 2011, 13 pages.

* cited by examiner

DEVICES, SYSTEMS, AND METHODS FOR DETECTING ODORANTS

CROSS-REFERENCE TO RELATED APPLICATIONS

This Application is a U.S. National Stage filing under 35 U.S.C. § 371 of International Application No. PCT/US2013/024887, filed on Feb. 6, 2013 entitled "DEVICES, SYSTEMS, AND METHODS FOR DETECTING ODORANTS" which is incorporated herein by reference in its entirety.

BACKGROUND

Among sensors corresponding to the five human senses (sight, hearing, touch, taste, and smell), sensors associated with sight, hearing, and touch, which utilize physical stimuli, have been put to practical use and have come to be used, for example, in mobile devices. However, there has been little progress in providing such mobile devices with sensors associated with taste or smell. Such lack of technical progress may be attributable to a lack of development of a small sensor element that can function as an odor sensor.

As one example, an odor sensor may be composed of a semiconductor gas sensor. However, a typical size of such a semiconductor sensor may be at least about 1 cm, which may reduce its usefulness in a small device. Furthermore, considerable electric power may be required to power a semiconductor gas sensor. Due to its size, this type of odor sensor may be applicable for use in stationary devices, but may not be suitable for use in mobile devices such as cell phones that are powered by batteries.

It is therefore clear that a need exists for a device, system, and method for detecting odorants, capable of being housed in a small portable device.

SUMMARY

In an embodiment, a device for sensing one or more odorants may include an oscillator crystal having a first side, a first conductive film in electrical communication with the first side of the oscillator crystal, and a first polymer coating in physical communication with the first conductive film, in which the first polymer coating has a first diffusivity constant for a first odorant, a second diffusivity constant for a second odorant, and the first diffusivity constant is different than the second diffusivity constant.

In an embodiment, a system for sensing an odorant may include at least one device configured to sense one or more odorants. The device configured to sense one or more odorants may include an oscillator crystal having a first side and a second side, a first conductive film in electrical communication with the first side of the oscillator crystal, a second conductive film in electrical communication with the second side of the oscillator crystal, a first conductor in electrical communication with the first conductive film, a second conductor in electrical communication with the second conductive film, and a first polymer coating in physical communication with the first conductive film, in which the first polymer coating has a first diffusivity constant for a first odorant, a second diffusivity constant for a second odorant, and the first diffusivity constant is greater than the second diffusivity constant. The system may also include an oscillator circuit having at least one first circuit input and at least one first circuit output, in which the at least one first circuit input is in electrical communication with the first conductor and the at least one first circuit output is in electrical communication with the second conductor. Additionally, the system may include an electrical system in data communication with the oscillator circuit and configured to at least measure an oscillation frequency emitted by the oscillator crystal.

In an embodiment, a method of sensing an odorant may include providing a system for sensing an odorant, exposing the system for sensing an odorant to an amount of at least one odorant, measuring, using an electrical system component of the system for sensing the odorant, at least one oscillation frequency signal emitted by an oscillator crystal component of the system for sensing the odorant, identifying, using the electrical system, the odorant based at least in part on the at least one oscillation frequency signal, and determining, using the electrical system, the amount of the at least one odorant based at least in part on the at least one oscillation frequency signal. The system for sensing an odorant may include at least one device for sensing one or more odorants, an oscillator circuit having at least a first circuit input and at least a first circuit output, in which the first circuit input may be in electrical communication with a first conductor of the device for sensing one or more odorants, and the first circuit output is in electrical communication with a second conductor of the device for sensing one or more odorants, and an electrical system in data communication with the oscillator circuit and configured to at least measure an oscillation frequency emitted by an oscillator crystal component of the device for sensing one or more odorants. The device for sensing one or more odorants may include an oscillator crystal having a first side and a second side, a first conductive film in electrical communication with the first side of the oscillator crystal, a second conductive film in electrical communication with the second side of the oscillator crystal, a first conductor in electrical communication with the first conductive film, a second conductor in electrical communication with the second conductive film, and a first polymer coating in physical communication with the first conductive film. In addition, the first polymer coating of the device for sensing one or more odorants, may have a first diffusivity constant for a first odorant, a second diffusivity constant for a second odorant, and the first diffusivity constant is greater than the second diffusivity constant.

DETAILED DESCRIPTION

Figure 1A:
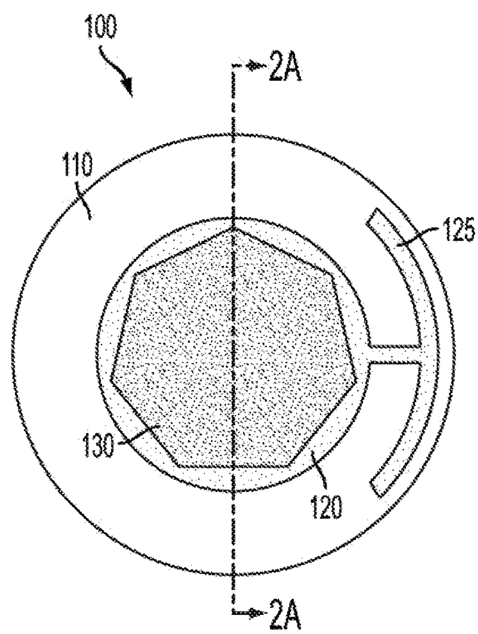
FIGS. 1A-D illustrate plan views of embodiments of a device for sensing one or more odorants in accordance with the present disclosure.
Figure 1B:
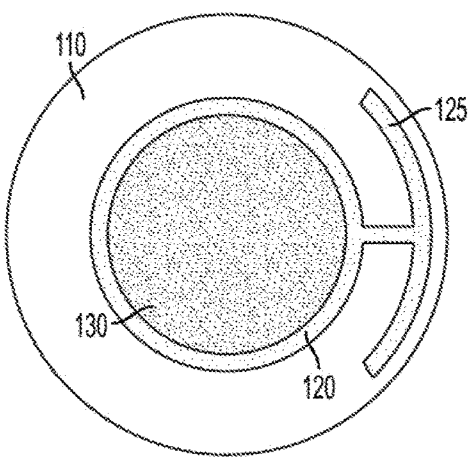
Figure 1C:
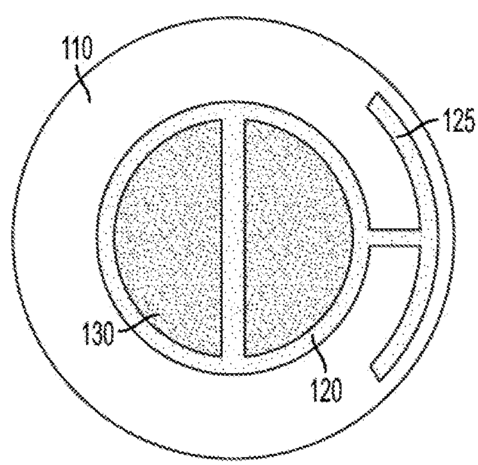
Figure 1D:
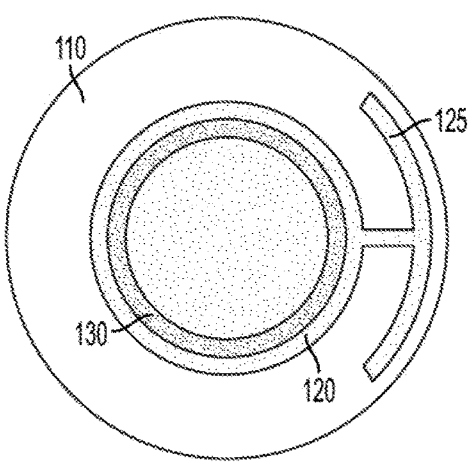

At least one type of odor sensor has been developed to mimic in some fashion the olfactory tissue of animals, specifically the nasal tissue. Such tissue may incorporate olfactory receptor neurons in the olfactory epithelium. The olfactory epithelium is typically coated with a thin mucosal protective layer through which odorants may pass before contacting the olfactory neuron cilia. The cilia may express receptors generally specific to a particular odorant. In some research, an electrode surface of an oscillator crystal has been coated with a lipid coating to mimic the combination of mucosal layer and the lipid bilayer of the receptor cells. Odorants that can pass through the lipid, sometimes fabricated as a cell-like lipid bilayer, may alter the properties of the oscillator crystal, thereby changing the crystal resonant frequency. However, such lipids may readily flow away and detach from the electrode surface. Additionally, without the use of any antimicrobial material added to the lipid, bacteria may associate with the lipid and metabolize it, thereby breaking down the crystal coating. Certain lipids, especially unsaturated lipids, may oxidize and degrade under nominal environmental conditions. Thus, for at least these reasons, a lipid-coated crystal may not produce a long-term stable output.

Alternative research has focused on a sensor incorporating a film formed of an odorant-adsorbing material that may be coated on an electrode surface of an oscillator crystal. A specific odorant may be identified by such a sensor based on a neural network analysis of the response signals generated by interactions of odorants and multiple types of films. However, a neural network-based analysis may require complex calculations using the response signals, and the resultant identification may be imprecise. Furthermore, as the number of possible odorants to be analyzed increases, the computational load due to the analysis may become considerable. The additional complexity due to multiple odorants may result in the need for increased parameter memory. The combination of computational overhead and required additional memory may make such an application impractical for the use in mobile devices. Additionally, without proper training, a neural network may become "brittle" and unable to resolve complex mixtures in a real-world application. It may thus be appreciated that an odorant sensing device that does not require an elaborate neural-network based analysis may be useful for incorporation into a small hand-held device.

As disclosed herein, an odorant sensing device may be fabricated by placing a polymer coating on a conductive film electrode in electrical communication with an oscillator crystal. Such a polymer coating may be characterized in part by the diffusivity constant of an odorant through the polymer. It may be appreciated that a particular odorant may have one diffusivity constant through one polymer but have a different diffusivity constant through a second polymer. Alternatively, a particular polymer may have a first diffusivity constant for a first odorant, but another diffusivity constant for a second odorant. As one example, isoamyl acetate (odor of bananas) may have a diffusivity constant of about $0.77\times10^{-8}$ $cm^2/sec$ through low density polyethylene and a diffusivity constant of about $0.0068\times10^{-8}$ $cm^2/sec$ through polypropylene. As another example, phenyl ethyl alcohol (odor of roses) may have a diffusivity constant of about $0.42\times10^{-8}$ $cm^2/sec$ through low density polyethylene and a diffusivity constant of about $0.0026\times10^{-8}$ $cm^2/sec$ through polypropylene. The diffusivity constant of an odorant through a particular polymer may be related to the amount of odorant adsorbed by the polymer over a period of time. As more odorant is adsorbed by a polymer coating an oscillator crystal, the total mass of the coated crystal may increase due to the added odorant material. As a result, the change in coated crystal mass may alter the natural frequency of the crystal, which in turn may be detected by additional electronic components. It may be appreciated, therefore, that an odorant sensor incorporating a polyethylene film or an odorant sensor incorporating a polypropylene film may be used to distinguish phenyl ethyl alcohol and isoamyl acetate, as non-limiting examples of odorants.

In some embodiments, the oscillator crystal may be composed of a piezoelectric material. In another embodiment, the oscillator crystal may be composed of one of a quartz crystal or a piezoelectric ceramic. Non-limiting examples of quartz crystal types that may be used as part of the sensor device may include an AT cut quartz crystal, an SC cut quartz crystal, a BT cut quartz crystal, an IT cut quartz crystal, an FC cut quartz crystal, an AK cut quartz crystal, a CT cut quartz crystal, a DT cut quartz crystal, an SL cut quartz crystal, a GT cut quartz crystal, an E cut quartz crystal, an MT cut quartz crystal, an ET cut quartz crystal, an FT cut quartz crystal, an NT cut quartz crystal, an H cut quartz crystal, a J cut quartz crystal, an RT cut quartz crystal, an SBTC cut quartz crystal, a TS cut quartz crystal, an X 30° cut quartz crystal, an LC cut quartz crystal, an AC cut quartz crystal, a BC cut quartz crystal, an NLSC cut quartz crystal, a Y cut quartz crystal, and an X cut quartz crystal.

A conductive film may form an electrode placed on a surface of the crystal. A conductor may also be included to enable electrical connectivity between additional electrical components and the electrode. It may be appreciated that an oscillator crystal may have separate conductive films applied to each of a front surface and a rear surface of the oscillator crystal, thereby forming a pair of electrodes. Similarly, separate conductors may be placed on each of the front surface and the rear surface of the crystal to permit electrical contact between external electrical components and the respective front and rear electrodes. Non-limiting examples of the conductive film may include one or more of gold, silver, titanium, platinum, copper, aluminum, and palladium. It may be appreciated that the conductive film applied to a first side of the oscillator crystal and the conductive film applied to the second side of the oscillator crystal may be made of the same material or different materials. It may also be appreciated that conductors in electrical communication with the conductive films may be made of the same material as the films or different materials. It may also be appreciated that the shape, size, thickness, and disposition of the conductive film electrode and/or conductor on one side of the oscillator crystal may be the same as or different from those of the conductive film electrode and/or conductor on the second side of the oscillator crystal.

A polymer coating material may include one or more of a polyacrylic material, a polyester material, a polyolefin material, and a polyvinyl material. Non-limiting examples of the polymer coating may include one or more of polycaprolactone, polystyrene, cycloolefin, polycarbonate, polyolefin, polypropylene, polymethylmethacrylate, polyvinyl alcohol, and polyethylene terephthalate. The polymer coating may be dissolved in organic solvents so that they can be applied to one or more conductive film electrode surfaces. In some non-limiting embodiments, the polymer coating may be applied to a single conductive film electrode on one side of an oscillator crystal. In some alternative non-limiting embodiments, the polymer coating may be applied to the conductive film electrodes on both sides of an oscillator crystal. It may be appreciated that the polymer coating applied to a conductive film electrode on a first side of the oscillator crystal and the polymer coating applied to a conductive film electrode on a second side of the oscillator crystal may have the same composition or different compositions.

An amount of polymer coating deposited on a conductive film electrode of an oscillator crystal may be controlled by defining the concentrations of the polymer solutions and the amounts of solutions applied to the conductive film electrode, or by monitoring changes in the resonant frequencies of an oscillator crystal before and after the application of the coating. It may be understood that a change in oscillator crystal frequency may be dependent on the amount of polymer material coating the one or more conductive film electrodes. In some non-limiting embodiments, a polymer coating may incorporate an amount of polymer material over an electrode surface area of about 0.4 fg/$\mu m^2$ to about 90 fg/$\mu m^2$. Non-limiting examples of the amount of polymer material coated on one or both sides of an oscillator crystal may include about 0.4 fg/$\mu m^2$, about 0.5 fg/$\mu m^2$, about 1 fg/$\mu m^2$, about 2 fg/$\mu m^2$, about 4 fg/$\mu m^2$, about 5 fg/$\mu m^2$, about 10 fg/$\mu m^2$, about 20 fg/$\mu m^2$, about 40 fg/$\mu m^2$, about 60 fg/$\mu m^2$, about 80 fg/$\mu m^2$, about 90 fg/$\mu m^2$, or ranges between any two of these values. In one non-limiting example, the polymer coating may comprise about 4 fg/$\mu m^2$ of a polymer material.

A syringe, pipette, inkjet dispenser, or jet dispenser may be used to coat the polymer on the conductive film electrodes in one or more layers. The polymer solutions may be applied in various fashions to form layers having a variety of shapes. In one non-limiting embodiment, the polymer coating may have a thickness of about 0.4 nm to about 90 nm. Non-limiting examples of the thickness of polymer material coated on one or both sides of the conductive film electrode of an oscillator crystal may include about 0.4 nm, about 0.8 nm, about 1 nm, about 2 nm, about 4 nm, about 5 nm, about 10 nm, about 20 nm, about 40 nm, about 60 nm, about 80 nm, about 90 nm, or ranges between any two of these values. In one non-limiting example, the polymer coating may have a thickness of about 4 nm.

In addition, the sensor device may include one or more layers of polymer coating on the conductive film electrode on one or both sides of oscillator crystal. In one non-limiting example, the polymer coating may include a single layer of polymer material. In another non-limiting example, the polymer coating may include multiple layers of one or more polymer materials. In some non-limiting embodiments, the polymer coating may include about 2 polymer layers to about 10 polymer layers of one or more polymer materials. Non-limiting examples of the number of polymer material layers coated on the conductive film electrode of one or both sides of an oscillator crystal may include about 2 layers, about 3 layers, about 4 layers, about 5 layers, about 6 layers, about 7 layers, about 8 layers, about 9 layers, or about 10 layers. In one embodiment, the polymer coating may include about 2 layers of one or more polymer materials. In some non-limiting embodiments, the number of polymer layers together may have a total thickness of about 0.8 nm to about 900 nm. Non-limiting examples of the total thickness of multiple polymer layers on one or both sides of the conductive film electrode of an oscillator crystal may include about 0.8 nm, about 1.6 nm, about 2 nm, about 4 nm, about 5 nm, about 10 nm, about 20 nm, about 40 nm, about 60 nm, about 80 nm, about 100 nm, about 200 nm, about 400 nm, about 600 nm, about 800 nm, about 900 nm, or ranges between any two of these values. In one non-limiting example, the number of polymer layers together may have a total thickness of about 900 nm. It may be understood that one or more polymer layers comprising a polymer coating may have any of a variety of shapes, non-limiting examples being a disk, a ring, a wheel, a quadrilateral, a triangle, a polygon, a pyramid, a cube, a cone, an ellipse, a cross, a grid, a cylinder, and a hemisphere.

It may be appreciated that the two sides of an oscillator crystal may have the same or different numbers of layers of polymer material in the coatings. It may also be appreciated that the layers of polymer material placed on the conductive film electrode on a first side of the oscillator crystal may have essentially the same shape, thickness, and composition of polymer material as those placed on the conductive film electrode on a second side of the oscillator crystal. Alternatively, the layers of polymer material on a first side of an oscillator crystal may differ in one or more of their shape, thickness, and/or concentration of polymer material from those on a second side of the oscillator crystal.

FIGS. 1A-D and 2A-E illustrate some embodiments of odorant sensing devices 100 including an oscillator crystal 110 having one or more polymer coatings 130 placed on conductive film electrode surfaces 120. The conductive film electrodes 120 and conductors 125 may be fabricated as separate components or together in one process step. FIGS. 1A-E illustrate plan views of such odorant detecting devices 100. While the cross-sectional view 2A as illustrated in FIGS. 2A-E may be referenced to FIG. 1A, it may be understood that similar cross-sections may also be obtained referencing any of the other FIGS. 1B-D. Thus, in one embodiment, illustrated by FIG. 1A, the polymer coating 130 may include any of a number of regular or irregular polygons. In one embodiment, illustrated by FIG. 1B, the polymer coating 130 may include any of a number of curved geometric shapes, such as a circular shape, ellipses, or ovals. In still another embodiment, illustrated by FIG. 1C, the polymer coating 130 may include multiple separate geometric shapes, such as paired semi-circles. In yet another embodiment, illustrated by FIG. 1D, the polymer coating 130 may include only a portion of the area of a geometric shape, such as a ring.

Figure 2A:
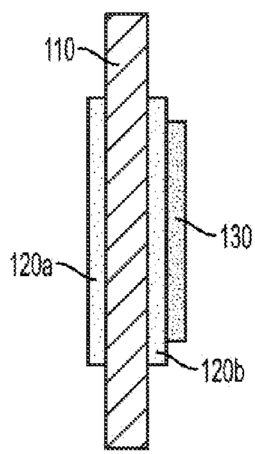
FIGS. 2A-E illustrate cross-sectional views of embodiments of a device for sensing one or more odorants in accordance with the present disclosure.
Figure 2B:
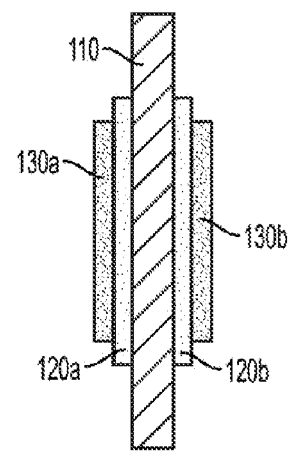
Figure 2C:
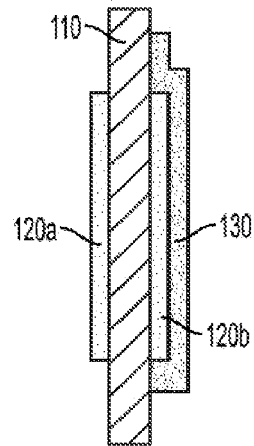
Figure 2D:
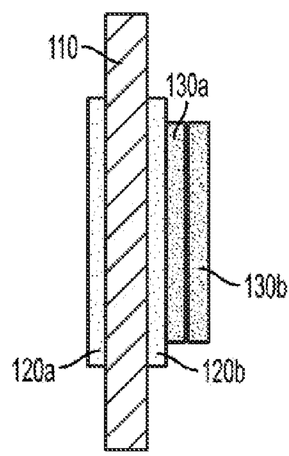
Figure 2E:
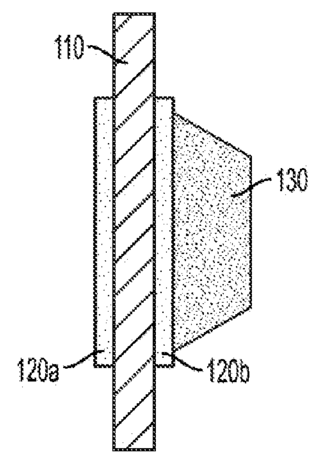

FIGS. 2A-E illustrate some additional embodiments of such odorant sensing devices, shown in a cross-sectional view, such as cross-section 2A through the device illustrated in FIG. 1A. In one embodiment, illustrated by FIG. 2A, the polymer coating 130 may be applied only to one conductive film electrode 120*b* of the two conductive film electrodes 120*a,b* of a crystal 110. In another embodiment, illustrated in FIG. 2B, polymer coatings 130*a,b* may be applied to each of the two conductive film electrodes 120*a,b*, respectively, of a crystal 110. It may be appreciated that polymer coating 130*a* may be the same as or different than polymer film coating 130*b*. In one example, polymer coating 130*a* may have a different concentration of polymer than polymer coating 130*b*. In another example, polymer coating 130*a* may have a different shape and/or size than polymer coating 130*b*. In yet another example, polymer coating 130*a* may comprise a different polymer than polymer coating 130*b*. As illustrated in FIG. 2C, a polymer coating 130 may also be placed in contact directly with the oscillator crystal 110 in addition to the thin conductive film electrode 120. FIG. 2D illustrates an embodiment in which multiple polymer coatings, 130*a,b*, may be placed on a single electrode 120*b*. Additionally, as illustrated in FIG. 2E, the polymer coating 130 may constitute a more complex three-dimensional shape than a simple single-thickness layer. Such shapes may include, without limitation, a truncated cone (as shown), a pyramid, a pyramidal prism, a cylinder, a portion of a sphere, or other three-dimensional shapes.

It should be appreciated that only a small number of a possible variety of geometries are illustrated in FIGS. 1A-D and 2A-E. The figures should not be taken as limiting any of the possible combinations of shapes, positioning, number of layers, layer thickness, or other attributes of the polymer coatings on the conductive film electrodes of the oscillator crystals, all of which may be encompassed by this disclosure.

The oscillator crystal frequency response to an odorant may depend on the type of polymer material applied, and the response sensitivity may be controlled by the amount and shape of the applied polymer material. By defining the types, amounts, and shapes of the applied polymer materials to the odorant sensing device, it may be possible to detect and identify odor components based on the frequency response characteristics of the crystals.

A coated oscillator crystal of an odorant sensing device as disclosed above may require exposure to a gaseous or vaporous odorant in order to provide odorant data. It may be realized, however, that the small crystal size of the oscillator crystal may make it too fragile for use in a portable device. Therefore, such a coated oscillator crystal may require a housing to enclose the oscillator crystal to protect it from physical damage. In one embodiment, an oscillator crystal housing may be composed of an electrically conductive material such as a metal. The electrically conductive material may be configured to effectively shield the oscillator crystal from a stray capacitance. The oscillator crystal housing may have an inside and an outside as well as a number of voids or holes in the housing to permit an odorant on the outside of the housing to enter the inside of the housing and thus be detected by the odorant sensor. As one non-limiting example, the voids in the oscillator housing may be fabricated from an electrically conductive mesh.

Odorant sensing devices composed of a polymer coated oscillator crystal, as disclosed above, may be incorporated into odorant sensing systems. One component of an odorant sensing system may include an oscillator circuit that may incorporate a polymer coated oscillator crystal. Such oscillator circuits may have at least one input in electrical communication with a first odorant sensing device conductor and at least one output in electrical communication with a second odorant sensing device conductor. Oscillator circuits may be used to provide a voltage output having a frequency component determined at least in part by the frequency emitted by the coated oscillator crystal.

Figure 3A:
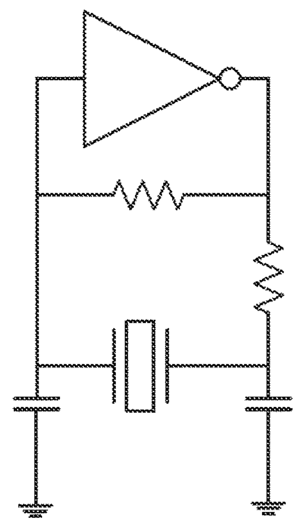
FIGS. 3A-C illustrate embodiments of an oscillator circuit in accordance with the present disclosure.
Figure 3B:
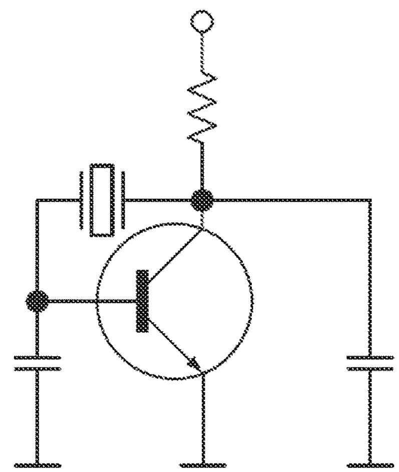
Figure 3C:
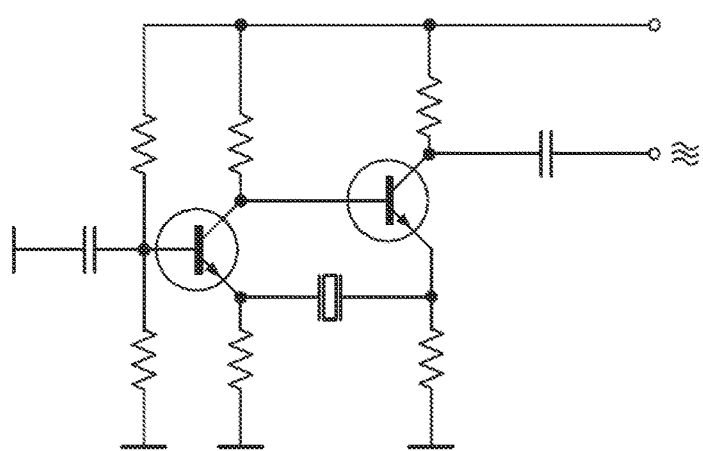

The oscillator circuit may comprise any number of a variety of circuits. In some embodiments, the oscillator circuit may include a digital circuit, an analog circuit, or a combination analog and digital circuit. FIG. 3A, for example, illustrates a mixed analog and digital circuit, including the coated crystal device, an inverter (digital component), and resistors and capacitors (analog components). Non-limiting examples of analog circuits are illustrated in FIGS. 3B and 3C. FIG. 3B, for example, illustrates a Pierce oscillator circuit, which is a form of parallel-resonance circuit. Other parallel resonant oscillator circuits may include a Colpitts oscillator circuit, or a Clapp oscillator circuit. FIG. 3C illustrates a Butler oscillator circuit, which is a form of series resonant oscillator circuit.

An oscillator circuit may further provide data in the form of a voltage having a frequency component to an electrical system capable of receiving and analyzing the oscillator circuit output frequency. FIGS. 4A-D illustrate non-limiting examples of odorant detecting systems including one or more odorant detectors and additional electrical systems.

Figure 4A:
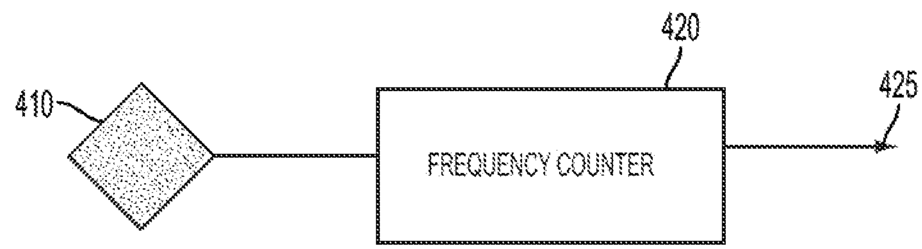
FIGS. 4A-D illustrate embodiments of some electronic components of a system for sensing an odorant in accordance with the present disclosure.

In one non-limiting embodiment of an electronic system, illustrated in FIG. 4A, an odorant detector 410, comprising an oscillator circuit and an odorant detector oscillator crystal, may provide at least one oscillation frequency signal that may be detected by a frequency counter 420. The oscillator circuit may be a mixed analog/digital circuit configured to provide a digital frequency signal output. The digital output may be detected by a digital frequency counter 420 that may provide a digital output 425 related to the input frequency. The digital output 425 may have any of a number of standard digital formats including parallel encoding and serial encoding.

Figure 4B:
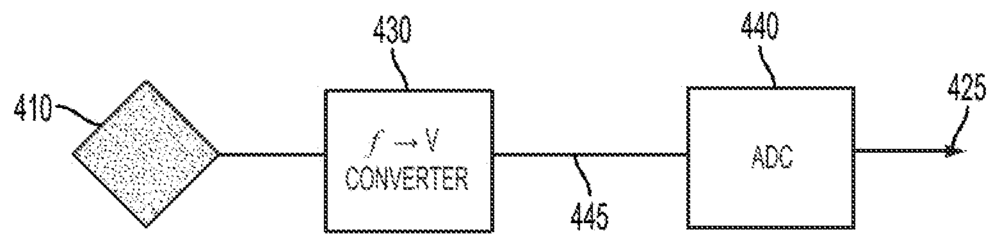

In one non-limiting embodiment of an electronic system, illustrated in FIG. 4B, an odorant detector 410 may provide at least one oscillation frequency signal that may be detected by a frequency-to-voltage (f-to-V) converter 430. The output of the f-to-V converter 430 may be an output analog signal 445 having a voltage proportional to the output frequency of the odorant detecting device. The analog signal 445 may be converted to a digital output 425 by means of an analog-to-digital converter (ADC) 440.

Figure 4C:
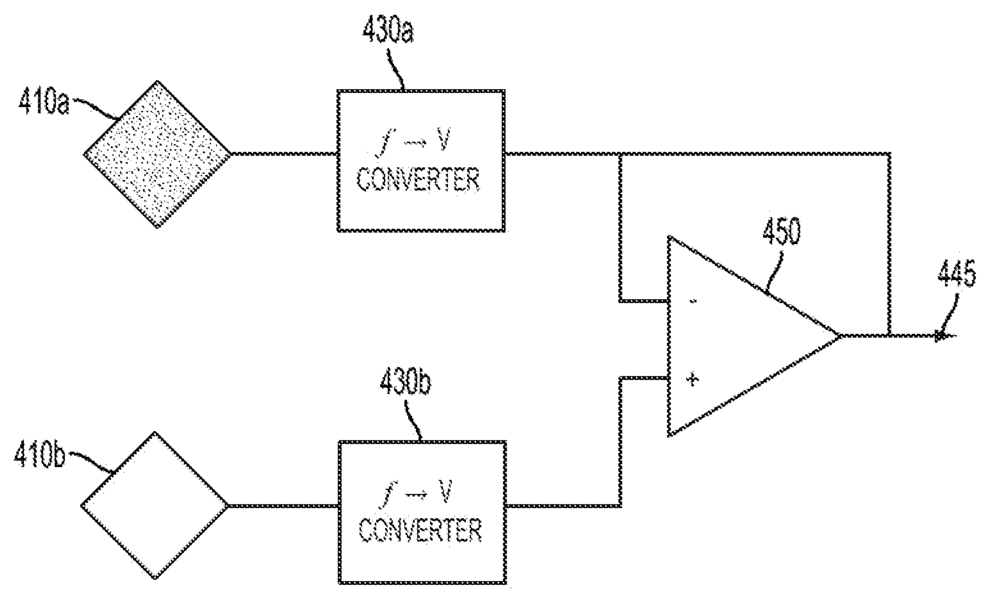

FIG. 4C illustrates yet another non-limiting embodiment of an electronic system that may incorporate the outputs of two odorant detectors 410*a,b*. In one example, a first odorant detector 410*a* may have a first configuration of a polymer coating and the second odorant detector 410*b* may have a different configuration of a polymer coating. The polymer coatings may differ in amount of polymer, polymer composition, or polymer coating geometry. In another example, the first odorant detector 410*a* may have a polymer coating while the second detector 410*b* may lack any coating. In still another example, the first odorant detector 410*a* may be secured in a housing allowing an odorant to be adsorbed onto the polymer coating. A second odorant detector 410*b*, having essentially the same polymer composition, amount, and geometry as the first odorant detector 410*a*, may be secured in a hermetically sealed housing, thereby preventing an odorant from being adsorbed on the coating. As illustrated in FIG. 4C, each odorant detector, 410*a* or 410*b*, may provide an output voltage to a separate f-to-V converter, 430*a* or 430*b*, respectively. The voltage signals from the f-to-V converters, 430*a* and 430*b*, may serve as positive and negative inputs for a differential amplifier 450. The differential amplifier, which may include a low noise instrumentation amplifier, may produce an analog output 445 proportional to the difference between the frequency signals emitted by each of the two odorant detectors 410*a* and 410*b*. In this manner, one odorant detector, for example 410*b*, may serve as a reference against which the other detector 410*a* may be measured. Alternatively, two odorant detectors, 410*a* and 410_b_, each having a different polymer coating characteristic, may be able to resolve a specific odorant and/or its concentration.

Figure 4D:
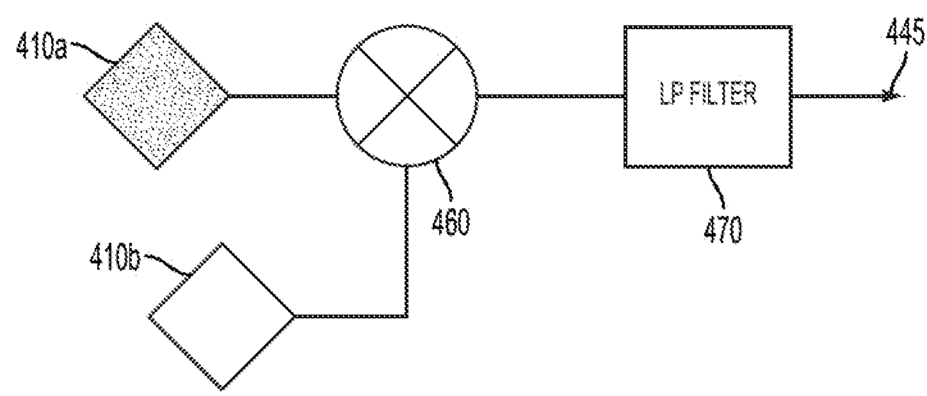

FIG. 4D illustrates still another non-limiting embodiment of an electronic system that may incorporate the outputs of two odorant detectors 410_a,b_. In one example, a first odorant detector 410_a_ may have a first configuration of a polymer coating and the second odorant detector 410_b_ may have a different configuration of a polymer coating. The polymer coatings may differ in amount of polymer, type of polymer, or polymer coating geometry. In another example, the first odorant detector 410_a_ may have a polymer coating while the second detector 410_b_ may lack any coating. In still another example, the first odorant detector 410_a_ may be secured in a housing allowing an odorant to be adsorbed onto the polymer coating, while the second odorant detector 410_b_ may be secured in a hermetically sealed housing, thereby preventing an odorant from being adsorbed on the coating. As illustrated in FIG. 4D, each odorant detector, 410_a_ or 410_b_, may provide an output voltage to a frequency mixer 460. One of the odorant detector outputs, for example from detector 410_b_, may serve as a reference frequency by which the signal from detector 410_a_ may be multiplied. The output signal from the mixer 460 may include signal components having the sum of the frequencies of the inputs and the difference of the frequencies of the inputs. A low pass filter 470 may then isolate the signal corresponding to the difference in frequencies between the outputs of detector 410_a_ and 410_b_. The low pass filter 470 may thus provide an analog signal output 445 characterized by essentially the difference in the detector output frequencies. It may be appreciated that the analog voltage output 445 from FIG. 4C may be digitized using an ADC 440 as in FIG. 4B. Similarly, the analog frequency signal 445 from FIG. 4D may be digitized using an analog frequency counter 420 as illustrated in FIG. 4A.

While several different electronic systems for odorant detection are illustrated in FIGS. 4A-D, it may be appreciated that such systems represent only a few possible systems that may be used to provide frequency data for additional analysis. Additional components may also be included in such systems, including but not limited to signal filters, signal processors, microprocessors, memory components, storage components of analysis software, and similar digital and/or analog components.

Figure 5:
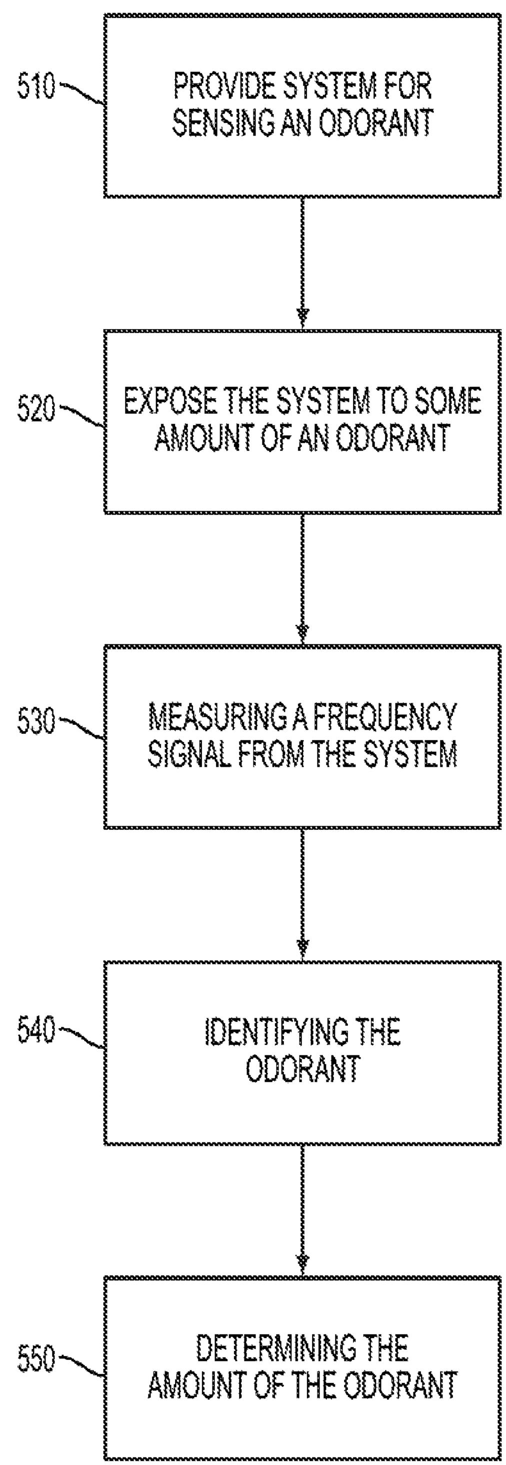
FIG. 5 is a flow chart of an embodiment of a method for sensing an odorant in accordance with the present disclosure.

FIG. 5 is a flow chart of one embodiment of a method for sensing and analyzing one or more odorants. A system essentially as disclosed above for sensing an odorant may be provided 510. Such a system may include one or more odorant sensing devices composed of a polymer coated oscillator crystal, one or more oscillator circuits in electrical communication with the one or more coated oscillator crystals, and additional electronics to measure and analyze one or more oscillation frequencies emitted by the one or more oscillator crystals.

The odorant sensing detector, alone or including any one or more components of the odorant sensing system, may be exposed to some amount of one or more odorants 520. Generally, any odorant or odorants can be detected by the odorant sensing detector. The odorant can be a single odorant, or a simple or complex mixture of two or more odorants. The one or more odorants may include a volatile organic compound, a solvent, a flavorant, a perfume, an amine, a thiol, a diamine, and/or a triamine. Non-limiting examples of such odorants may include one or more of acetone, trichloroethylene, phenylethyl alcohol, undecalactone, methanethiol, putrescine, cadaverine, butyric acid, butyric anhydride, indole, pyridine, skatole, trimethylamine, butyl seleno mercaptan, perchloroethylene, benzene, toluene, xylene, acetic acid, valeric acid, ethanol, butanol, and methanol.

The odorant sensing system may then measure a frequency signal derived from the odorant sensing detector 530. In some embodiments, the measurement may include at least one oscillation frequency signal emitted by at least oscillator crystal over a period of time. The measurement time period may have a starting point before the system is exposed to the odorant. Alternatively, the measurement time period may have a starting point after the system is exposed to the odorant. The at least one oscillator crystal frequency may be measured over a period of time of about 10 seconds to about 300 seconds Non-limiting examples of the period of time over which the at least one oscillator crystal frequency may be measured may include about 10 seconds, about 20 seconds, about 40 seconds, about 60 seconds, about 80 seconds, about 100 seconds, about 120 seconds, about 140 seconds, about 160 seconds, about 180 seconds, about 200 seconds, about 225 seconds, about 250 seconds, about 275 seconds, about 300 seconds, or ranges between any two of these values. In one non-limiting example, the period of time for making the frequency measurement may be about 120 seconds Alternatively, the frequency may be measured 530 over one or more short periods of time at one or more known time intervals after the odorant detector has been exposed to the one or more odorants.

In one non-limiting embodiment, measuring 530 at least one oscillation frequency signal may include measuring a first frequency emitted by the oscillator crystal in the absence of the odorant, measuring a second frequency emitted by the oscillator crystal in the presence of the odorant, and calculating a difference between the first measured frequency and the second measured frequency. In another non-limiting embodiment, measuring 530 at least one oscillator crystal signal may include measuring an oscillator frequency from a first crystal detector, measuring a frequency from a second crystal detector and making a comparison between the two measurements. In one non-limiting example, the two oscillator crystals may have a polymer coating with the same material composition, but having different configurations (such as shape, polymer concentration, or number of layers). In another non-limiting example, the two oscillator crystals may have the same polymer coatings with the same configuration, but the first odorant detector may be exposed to the odorant while the second odorant detector may be isolated from the odorant. In yet another non-limiting example, the two odorant detectors may have polymer coatings of different composition.

In another non-limiting embodiment, measuring 530 at least one oscillation frequency signal may also include measuring the amplitude of the at least one oscillation frequency signal. In some non-limiting examples, the measured frequency signal amplitude may be the peak-to-peak amplitude of the frequency signal, or the root-mean-squared amplitude of the frequency signal.

Based on the one or more frequency signals obtained from the odorant sensing system, the nature or composition of the odorant may be identified 540, and the amount of the odorant, for example as parts per million, may be determined 550.

In some non-limiting embodiments, identifying the composition or nature of an odorant may include extracting, by the electronic device, at least one data component from one or more oscillation frequency signals and comparing, by the electronic device, the one or more data components to one or more look-up table values, including using an interpolation calculation as necessary. The look-up table values may be derived from experimental data or mathematical models. The look-up table may have one or more data values associated with one or more odorants. Non-limiting examples of one or more of such data components extracted from the one or more oscillation frequency signals may include an oscillator crystal frequency, a change in oscillator crystal frequency, a rate of change of the oscillator crystal frequency, an amplitude of an oscillator crystal frequency, or a change in phase of the oscillator crystal frequency. In an alternative embodiment, identifying the odorant may include extracting, by the electronic device, one or more data components from one or more oscillation frequency signals and comparing, by the electronic device, the one or more data components to at least one data value derived from a mathematical model. The one or more data components extracted from the oscillation frequency signal(s) may include, without limitation, the data components as disclosed above.

In some non-limiting embodiments, identifying the amount of odorant may include extracting, by the electronic device, at least one data component from one or more oscillation frequency signals and comparing, by the electronic device, the one or more data components to one or more look-up table values, including using an interpolation calculation as necessary. The look-up table values may be derived from experimental data or mathematical models. The look-up table may have one or more data values associated with the amount of one or more odorants. Non-limiting examples of one or more of such data components extracted from the one or more oscillation frequency signals may include an oscillator crystal frequency, a change in oscillator crystal frequency, a rate of change of the oscillator crystal frequency, an amplitude of an oscillator crystal frequency, or a change in phase of the oscillator crystal frequency. In another embodiment, identifying the amount of odorant may also include, at least in part, using the composition or nature of the odorant as determined by the odorant sensing system. In an alternative embodiment, identifying the amount of odorant may include extracting, by the electronic device, one or more data components from one or more oscillation frequency signals and comparing, by the electronic device, the one or more data components to at least one data value derived from a mathematical model. The one or more data components extracted from the oscillation frequency signal(s) may include, without limitation, the data components as disclosed above.

EXAMPLES

Figure 6A:
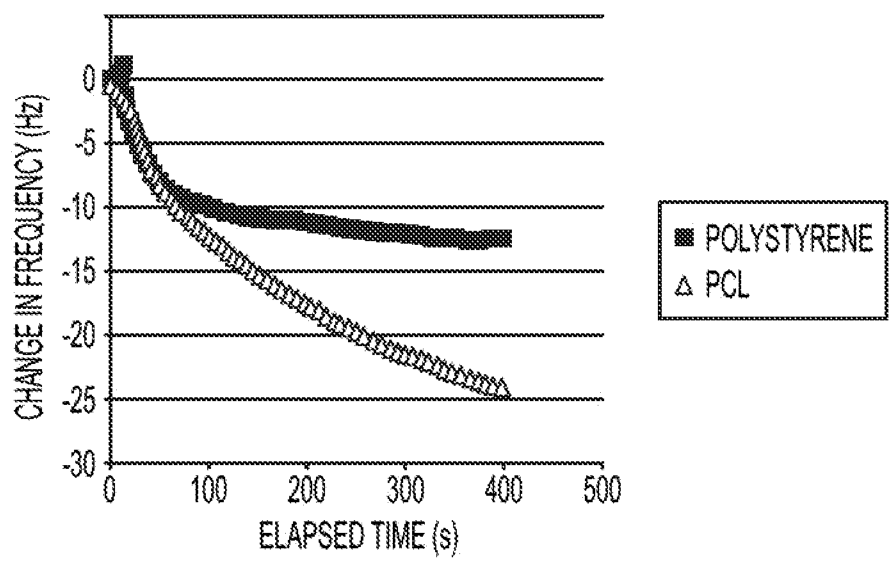
FIGS. 6A and B illustrate experimental results of the responses of two embodiments of a device for sensing one or more odorants (differing polymer compositions) to exposure to two different odorants in accordance with the present disclosure.
Figure 6B:
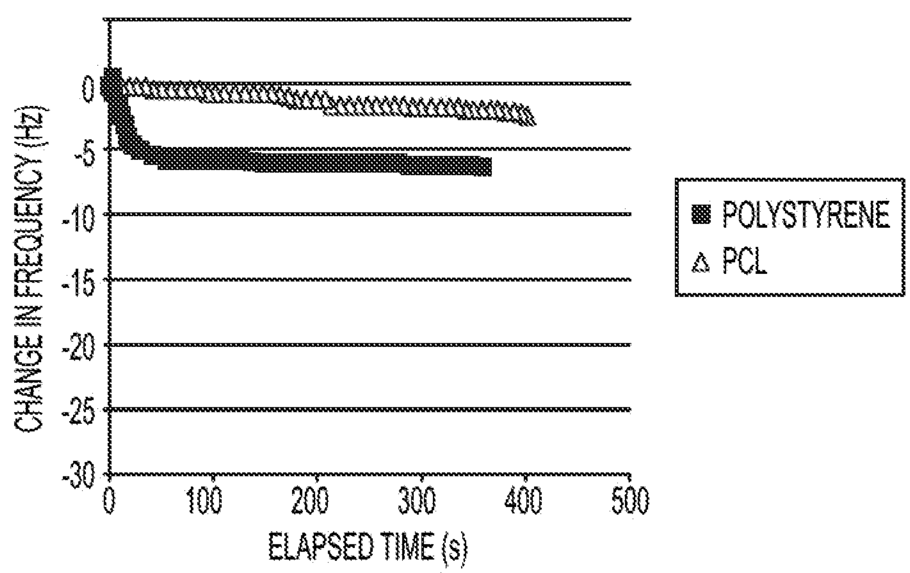

Example 1: Responses of Devices for Sensing Odorants to the Presence of Two Different Odorants FIGS. 6A and 6B illustrate some examples of dynamic responses of devices for sensing odorants as disclosed above. In both figures, the sensing devices included a disk-shaped, AT-cut quartz oscillator crystal having vapor-deposited gold electrodes applied as conductive films on the opposing sides of the crystals. The natural frequency of the crystals was about 9 MHz. The oscillator circuits were essentially the same as illustrated in FIG. 3A with the addition of a second inverter at the outputs. The oscillator circuit frequencies were measured using a frequency counter. One of the devices was coated with a film of polycaprolactone (PCL), while the other device was coated with a film of polystyrene. The films were formed by dissolving the polymer in a solvent at a concentration of about 60 ng/μL. The solutions were applied primarily to the surfaces of the gold electrodes. It may be noted that the crystals including the polymer coating demonstrated a negative frequency shift of about 600 Hz with respect to the uncoated crystals. The post-coating frequency may be considered a baseline frequency for the purpose of measuring the effect of the odorant on the coated crystals.

FIG. 6A illustrates typical responses of the two types of odorant detector crystals to exposure to an odorant composed of phenylethyl alcohol (odor of roses). The odorant was diluted about 50-fold by volume in acetone to form a test solution. Each odorant detector was placed in a glass vessel of about 35 ml. The odorant was introduced as a 1 μL drop of the test solution applied to the head of a cotton swab, and the swab was placed in the vessel along with the odorant detector crystal.

FIG. 6A illustrates that a PCL coated detector produced a different response to the phenylethyl alcohol over about 6 minutes compared to the polystyrene-coated detector. Specifically, after about 6 minutes of exposure to the phenylethyl alcohol, the PCL-coated crystal demonstrate a frequency shift of about −24 Hz (compared to baseline) compared to the polystyrene-coated crystal that appeared to plateau in its response to about −12 Hz (compared to baseline).

FIG. 6B illustrates typical responses of the two types of odorant detector crystals to exposure to an odorant composed of undecalactone (odor of peaches). The odorant was diluted about 50-fold by volume in acetone to form a test solution. Each odorant detector was placed in a glass vessel of about 35 ml. The odorant was introduced as a 1 μL drop of the test solution applied to the head of a cotton swab, and the swab was placed in the vessel along with the odorant detector crystal.

FIG. 6B illustrates that the polystyrene-coated crystal responded more to undecalactone than did the PCL-coated crystal. It is noted that the frequency change in both crystals exposed to the undecalactone was not as great as the frequency changes measured in FIG. 6A (to the phenylethyl alcohol). Both odorant-sensing crystals demonstrated some response, although the response of the PCL-coated crystal appeared limited to about −2 Hz compared to baseline, while the polystyrene-coated crystal response appeared to plateau to about −6 Hz with respect to baseline. It may, therefore, be appreciated that the responses of an odorant sensing device to differing odorants may include both quantitative as well as qualitative differences.

Example 2: Odorant Concentration Responses of Devices for Sensing Odorants

Figure 7:
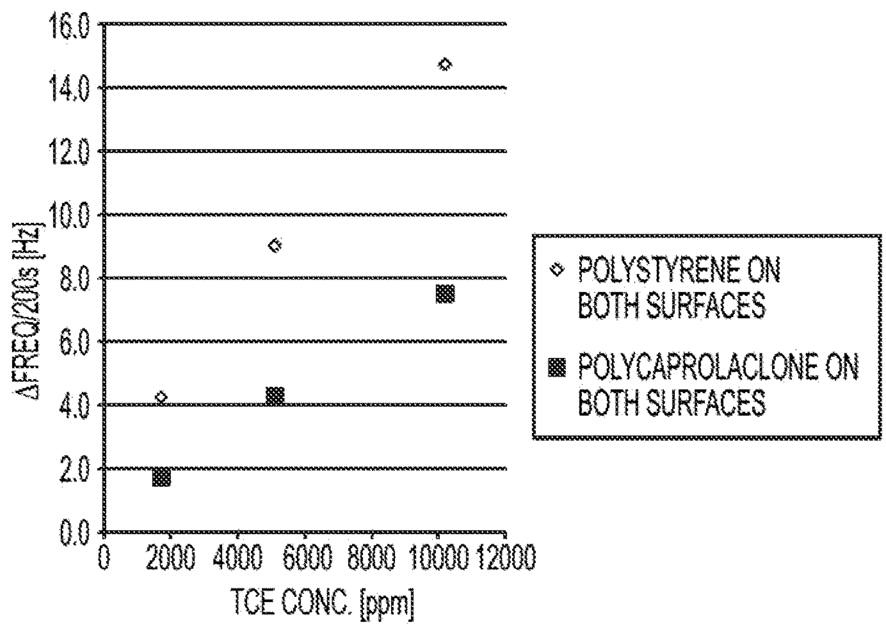
FIG. 7 illustrates experimental results of the responses of two embodiments of a device for sensing one or more odorants to exposure to a variety of concentrations of a volatile material in accordance with the present disclosure.

FIG. 7 illustrates some examples of the responses of two different embodiments of devices for sensing odorants as disclosed above to the concentration of a volatile oderant.

Trichloroethylene (TCE) was used as the odorant. A fixed quantity of trichloroethylene was added to a sealed glass bottle having an internal volume of 125 ml, and the bottle with TCE was warmed to about 80° C., thereby evaporating the TCE. A fixed volume of the test gas was extracted from the glass bottle with a syringe. The syringe was used to introduce the test gas into a second sealed glass container (the test vessel) in which polymer coated crystals were fixed. The polymer coated crystals were disk-shaped, AT-cut quartz oscillator crystals having vapor-deposited gold electrodes applied as conductive films on the opposing sides of the crystals. One of the polymer coated crystals was coated with five layers of polycaprolactone (PCL) on each of its two sides, while the other polymer coated crystal was coated with five layers of polystyrene on each of its two sides. The frequency of each polymer coated crystal was measured both before and after introduction of the test gas into the test vessel. The frequency of each of the polymer coated crystals was measured 200 seconds after the test gas was introduced into the test vessel. FIG. 7 illustrates graphs of the difference of the frequency response of each crystal against its baseline frequency after 200 seconds exposure to a variety of measured concentrations of TCE.

FIG. 7 illustrates an apparently linear response by both polystyrene-coated and PCL-coated crystals to odorant concentration. The slope of the response of the polystyrene-coated crystal was a change of about 1.4 Hz per 1000 ppm change in TCE concentration, while the slope of the PCL-coated crystal was a change of about 0.75 Hz per 1000 ppm change in TCE concentration. An odorant concentration dependent response of an odorant detecting device—such as a linear slope in a graph of detecting device frequency shift versus odorant concentration value—may be used as a means to distinguish between two or more odorants and/or the concentration of a specific odorant.

Figure 8:
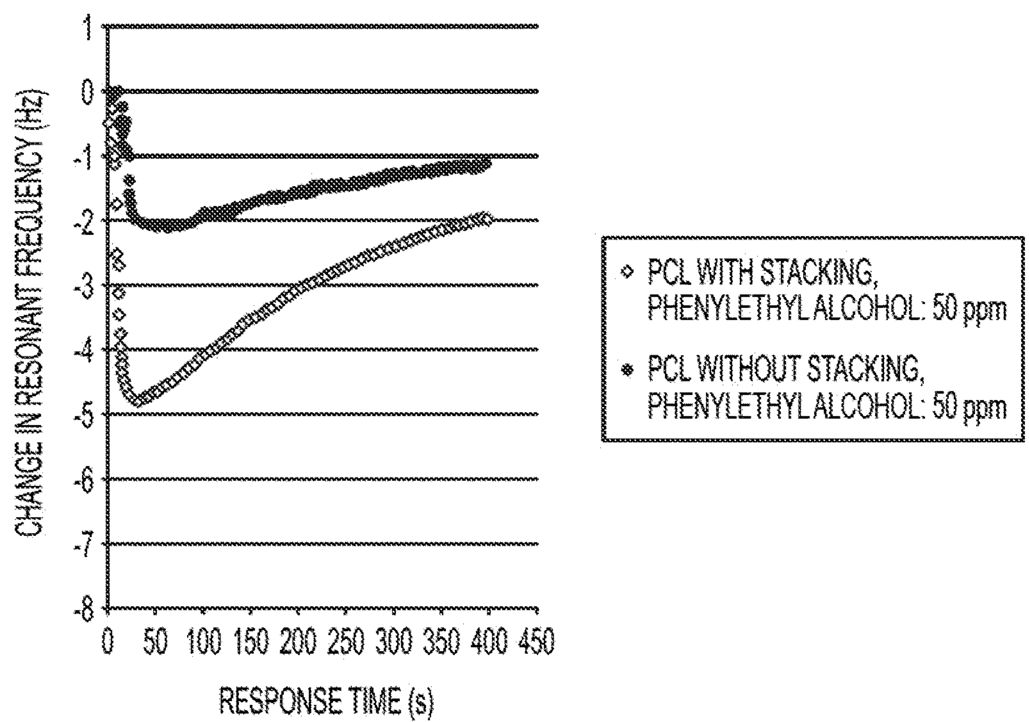
FIG. 8 illustrates experimental results of the responses of two embodiments of a device for sensing one or more odorants (differing number of polymer layers) to exposure to an odorant in accordance with the present disclosure.

Example 3: Dynamic Responses of Devices for Sensing Odorants Based on Polymer Configuration FIG. 8 illustrates examples of the responses of two different embodiments of devices for sensing odorants as disclosed above based on the disposition of the polymer film on the crystal electrode surface. Each of the two test devices was coated with a total of about 600 ng of PCL. In one device (listed in the legend of FIG. 8 as "without stacking"), the surface electrode on each side of the crystal was coated with a single polymer layer of about 1 cm in diameter and having about a 4 nm thickness. In the second device (listed in the legend of FIG. 8 as "with stacking"), the surface electrode on each side of the crystal was coated with five polymer layers, each layer about 3 mm in diameter and having about a 4 nm thickness. Each odorant sensing device was composed of a disk-shaped, AT-cut quartz oscillator crystal having vapor-deposited gold electrodes applied as conductive films on the opposing sides of the crystals. The devices were tested in a sealed test vessel and exposed to about 50 ppm phenylethyl alcohol within the test vessel.

FIG. 8 illustrates that the geometry of the polymer film, and not simply total polymer content, may have a significant effect on the odorant detecting device response. Specifically, at about 25 seconds after exposure to the odorant, the multi-layered device appears to respond about 2.5 times greater than the single-layered device. Without being bound by theory, it appears that the greater surface area afforded by the thin single layer device may lead to a reduced response as compared with that of a thicker multilayer device. It is conceivable that the rate of odorant adsorbed onto, and desorbed from, the polymer may be related to the amount of exposed polymer surface. Thus, a detector having a larger surface area may respond faster to exposure to an odorant. However, the amount of odorant retained by the polymer may be related to the thickness of the polymer layer. Thus, a detector having a thicker polymer surface layer may have a greater response to the odorant than one having a thinner polymer surface layer.

Example 4: Method of Identifying an Odorant and its Concentration

Figure 9A:
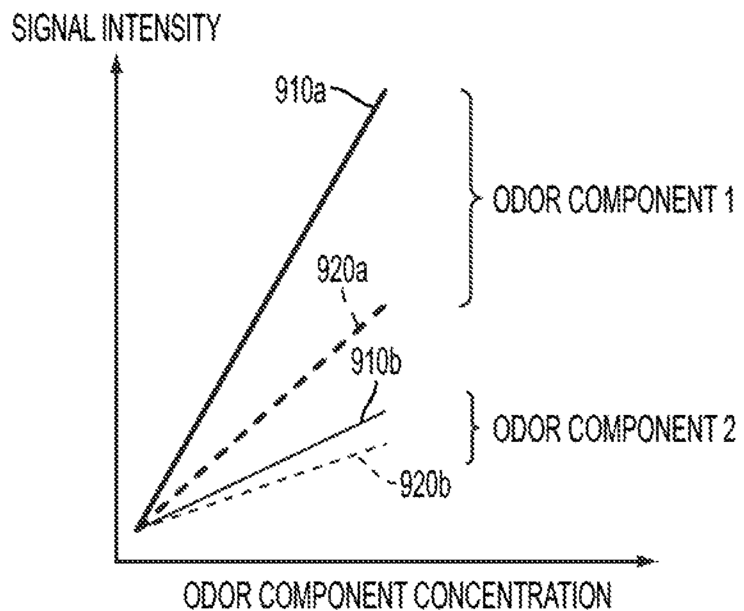
FIGS. 9A-C illustrate embodiments of a method of using a system for sensing an odorant to determine the identity and amount of an odorant in accordance with the present disclosure.
Figure 9B:
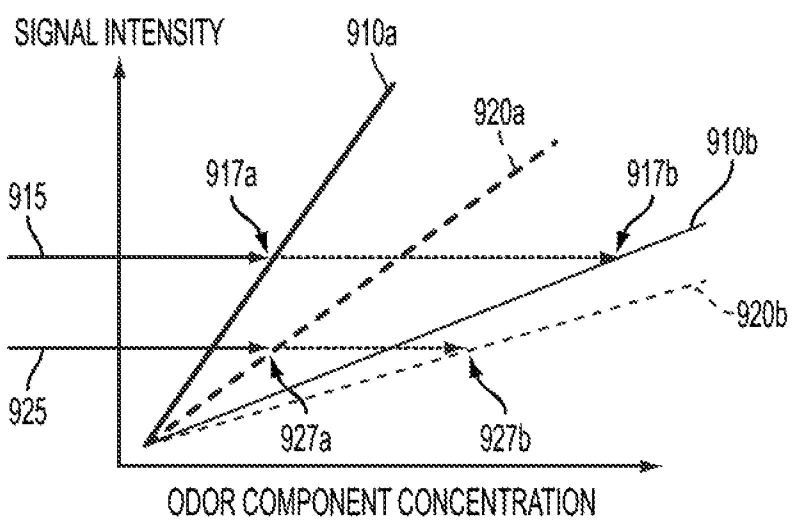
Figure 9C:
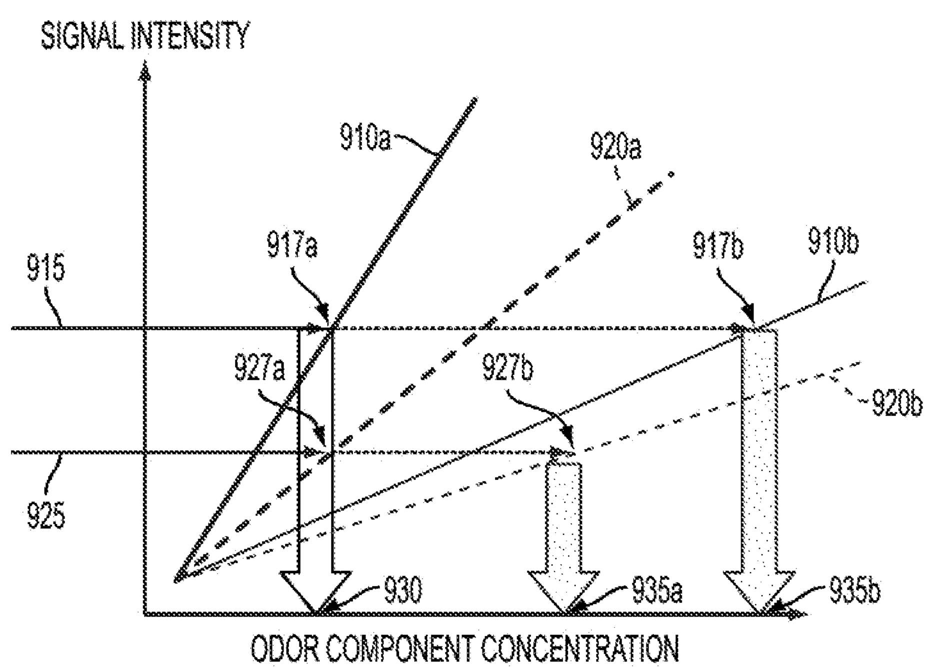

FIGS. 9A-C illustrate a non-limiting example of a method to determine an odorant composition as well as an amount of the odorant by an odorant detection system including two odorant detecting devices. FIG. 9A illustrates embodiments of possible response curves (910*a,b* and 920*a,b*) of two odorant detecting devices—a first device and a second device—to two different odorants (odor components 1 and 2). The odorant detecting system may be composed of two odorant detecting devices that may differ in one or more of their polymer coating material, polymer coating concentration, geometry of polymer coating, the number of layers of the polymer coatings, and/or the number of crystal surfaces to which the polymer coating is applied. For example, the two detecting devices may be composed of differing polymer coating materials, each having a different response to an odorant as illustrated in FIG. 7. Alternatively, the two detecting devices may be composed of differing numbers of polymer layers, each having a different response to an odorant as illustrated in FIG. 8. It may be appreciated that the detecting devices may have an odorant concentration range in which they each respond in a linear fashion to odorant concentration, as illustrated by the constant slopes of response curves 910*a* (for the first device) and 920*a* (for the second device) to odor component 1, and 910*b* (for the first device) and 920*b* (for the second device) to odor component 2. The response measured by the two odorant detecting devices may include one or more of the measurements disclosed above including, without limitation, a change in frequency, a rate of change in frequency, a change in signal amplitude, a rate of change in signal amplitude, a change in frequency phase and/or a rate of change in frequency phase.

The linear response curves 910*a,b* and 920*a,b* may be derived experimentally, by measuring the response of each device to known concentrations of one or more odorants. A graph of response versus concentration for each device may appear to be similar to the graph illustrated in FIG. 7. The individual values of detector response versus odorant concentration for each of the detectors may then be maintained in one or more databases. Alternatively, a linear response curve may be derived from a mathematical model of the measured response data. In one non-limiting example, linear response curves, each characterized by one or more model parameters, may be calculated from least-squares fits to experimental data such as presented in FIG. 7. The model parameters, such as slope and intercept, may then be used to calculate an estimated odorant concentration based on a detector's response to an odorant.

FIGS. 9B and 9C together illustrate a method in which an odorant detecting system composed of the two odorant detection devices having response characteristics as depicted in FIG. 9A may be used to distinguish an odorant as well as determine the odorant concentration. As disclosed above, with respect to FIG. 9A, first and second odorant detecting devices may have response curves to an odorant concentration, 910*a,b* and 920*a,b*, respectively, that differ in slope. Response curve 910*a* may be the response of the first detector to an odorant 1, and response curve 910*b* may be the response of the same detector to an odorant 2. Similarly, response curve 920*a* may be the response of the second detector to odorant 1, and response curve 920*b* may be the response of the same detector to odorant 2.

As depicted in FIG. 9B, the system, including, in part, the two detectors, may be exposed to some amount of an odorant. The first detecting device may produce a signal with a first intensity 915, while the second detecting system may produce a signal with a second intensity 925. If the odorant corresponds to odor component 1, then the intersection of first signal intensity 915 and the first odorant detector response curve to odorant 1 910*a* would be at point 917*a*. Alternatively, if the odorant corresponds to odor component 2, then the intersection of first signal intensity 915 and the first odorant detector response curve to odorant 2 910*b* would be at point 917*b*.

A similar analysis may be made for a possible response of the second detector to the odorant. Thus, if the odorant corresponds to odor component 1, the intersection of second signal intensity 925 and the second odorant detector response curve to odorant 1 920*a* would be at point 927*a*. Alternatively, if the odorant corresponds to odor component 2, then the intersection of second signal intensity 925 and the second odorant detector response curve to odorant 2 920*b* would be at point 927*b*.

FIG. 9C continues the analysis as disclosed above with respect to FIG. 9B. The first odorant detecting device, exposed to an odorant, may emit a signal with a first intensity 915, and a second odorant detecting device, exposed to the same odorant, may emit a signal with a second intensity 925. If the odorant corresponds to odorant 1, then the first detecting device may respond according to response curve 910*a* and the second detecting device may respond according to response curve 920*a*. Specifically, first signal intensity 915 may correspond to a value 917*a* on response curve 910*a*, and second signal intensity 925 may correspond to a value of 927*a* on response curve 920*a*. Alternatively, if the odorant corresponds to odorant 2, then the first detecting device may respond according to response curve 910*b* and the second detecting device may respond according to response curve 920*b*. Thus first signal intensity 915 may correspond to a value 917*b* on response curve 910*b*, and second signal intensity 925 may correspond to a value of 927*b* on response curve 920*b*.

It may be understood, that the two odorant detector devices would detect the same odorant at the same concentration. Therefore, it is reasonable to expect that the corresponding amount of odorant determined from the respective detector response curves should be consistent. As depicted in FIG. 9C, a first signal intensity 915 of the first detector may correspond to a value of 917*a* on the response curve to odorant 1 910*a*. The concentration of odorant 1, having a value 917*a* on the first device response curve 910*a*, may correspond to a concentration 930 for odorant 1. Alternatively, first signal intensity 915 may correspond to a value of 917*b* on the response curve to odorant 2 910*b*. The concentration of odorant 2 having a value 917*b* on the first device response curve 910*b* may correspond to a concentration 935*b* for odorant 2. Additionally, as depicted in FIG. 9C, a second signal intensity 925 of the second detector may correspond to a value of 927*a* on the response curve to odorant 1 920*a*. The concentration of odorant 1 having a value 927*a* on the second device response curve 920*a* may correspond to a concentration 930 for odorant 1. Alternatively, second signal intensity 925 may correspond to a value of 927*b* on the response curve to odorant 2 920*b*. The concentration of odorant 2, having a value 927*b* on the second device response curve 920*b*, may correspond to a concentration 935*a* for odorant 2. Since the two devices may be exposed to the same odorant at the same concentration, it is reasonable to expect that the unknown odorant would most likely correspond to odorant 1, since the responses of both detector devices result in consistent estimates for the odorant 1 concentration, but differ in their estimates of the concentration of odorant 2.

Although FIGS. 9A-C illustrate the ability of two separate odorant detector devices to resolve the identity and concentration of two odorants, it is reasonable to extend an odorant detecting system to include multiple detector devices. In such a manner, it may be appreciated that an odorant detecting system having "n" detectors may have the capability to resolve the concentration of "n" separate odorants.

The present disclosure is not to be limited in terms of the particular embodiments described in this application, which are intended as illustrations of various aspects. Many modifications and variations can be made without departing from its spirit and scope, as will be apparent to those skilled in the art. Functionally equivalent methods and apparatuses within the scope of the disclosure, in addition to those enumerated in this disclosure, will be apparent to those skilled in the art from the foregoing descriptions. Such modifications and variations are intended to fall within the scope of the appended claims. The present disclosure is to be limited only by the terms of the appended claims, along with the full scope of equivalents to which such claims are entitled. It is to be understood that this disclosure is not limited to particular methods, reagents, compounds, or compositions, which can, of course, vary. It is also to be understood that the terminology used in this disclosure is for the purpose of describing particular embodiments only, and is not intended to be limiting.

With respect to the use of substantially any plural and/or singular terms in this disclosure, those having skill in the art can translate from the plural to the singular and/or from the singular to the plural as is appropriate to the context and/or application. The various singular/plural permutations may be expressly set forth in this disclosure for sake of clarity. It will be understood by those within the art that, in general, terms used in this disclosure, and especially in the appended claims (e.g., bodies of the appended claims) are generally intended as "open" terms (e.g., the term "including" should be interpreted as "including but not limited to," the term "having" should be interpreted as "having at least," the term "includes" should be interpreted as "includes but is not limited to," etc.). While various compositions, methods, and devices are described in terms of "comprising" various components or steps (interpreted as meaning "including, but not limited to"), the compositions, methods, and devices can also "consist essentially of" or "consist of" the various components and steps, and such terminology should be interpreted as defining essentially closed-member groups.

It will be further understood by those within the art that if a specific number of an introduced claim recitation is intended, such an intent will be explicitly recited in the claim, and in the absence of such recitation no such intent is present. For example, as an aid to understanding, the following appended claims may contain usage of the introductory phrases "at least one" and "one or more" to introduce claim recitations. However, the use of such phrases should not be construed to imply that the introduction of a claim recitation by the indefinite articles "a" or "an" limits any particular claim containing such introduced claim recitation to embodiments containing only one such recitation, even when the same claim includes the introductory phrases "one or more" or "at least one" and indefinite articles such as "a" or "an" (e.g., "a" and/or "an" should be interpreted to mean "at least one" or "one or more"); the same holds true for the use of definite articles used to introduce claim recitations. In addition, even if a specific number of an introduced claim recitation is explicitly recited, those skilled in the art will recognize that such recitation should be interpreted to mean at least the recited number (e.g., the bare recitation of "two recitations," without other modifiers, means at least two recitations, or two or more recitations). Furthermore, in those instances where a convention analogous to "at least one of A, B, and C, etc." is used, in general such a construction is intended in the sense one having skill in the art would understand the convention (e.g., "a system having at least one of A, B, and C" would include but not be limited to systems that have A alone, B alone, C alone, A and B together, A and C together, B and C together, and/or A, B, and C together, etc.). It will be further understood by those within the art that virtually any disjunctive word and/or phrase presenting two or more alternative terms, whether in the description, claims, or drawings, should be understood to contemplate the possibilities of including one of the terms, either of the terms, or both terms. For example, the phrase "A or B" will be understood to include the possibilities of "A" or "B" or "A and B."

As will be understood by one skilled in the art, for any and all purposes, such as in terms of providing a written description, all ranges disclosed in this disclosure also encompass any and all possible subranges and combinations of subranges thereof. Any listed range can be easily recognized as sufficiently describing and enabling the same range being broken down into at least equal halves, thirds, quarters, fifths, tenths, etc. As a non-limiting example, each range discussed in this disclosure can be readily broken down into a lower third, middle third and upper third, etc. As will also be understood by one skilled in the art all language such as "up to," "at least," and the like include the number recited and refer to ranges which can be subsequently broken down into subranges as discussed above. Finally, as will be understood by one skilled in the art, a range includes each individual member.

From the foregoing, it will be appreciated that various embodiments of the present disclosure have been described for purposes of illustration, and that various modifications may be made without departing from the scope and spirit of the present disclosure. Accordingly, the various embodiments disclosed are not intended to be limiting, with the true scope and spirit being indicated by the following claims.

What is claimed is:

1. A device to sense one or more odorants, the device comprising:

an oscillator crystal having a first side and a second side;

a first conductive film in electrical communication with the first side of the oscillator crystal;

a second conductive film in electrical communication with the second side of the oscillator crystal;

a first conductor disposed on the first side of the oscillator crystal and in electrical communication with the first conductive film;

a second conductor in electrical communication with the second conductive film;

a first polymer coating in physical communication with the first conductive film; and a second polymer coating in physical communication with the second conductive film, wherein the first polymer coating has a different concentration than the second polymer coating, wherein the first polymer coating has a first diffusivity constant for a first odorant, and a second diffusivity constant for a second odorant, and wherein the first diffusivity constant is different than the second diffusivity constant.

2. The device of claim 1, wherein the oscillator crystal comprises one of a quartz crystal and a piezoelectric ceramic, and wherein the quartz crystal is selected from the group consisting of an AT cut quartz crystal, an SC cut quartz crystal, a BT cut quartz crystal, an IT cut quartz crystal, an FC cut quartz crystal, an AK cut quartz crystal, a CT cut quartz crystal, a DT cut quartz crystal, an SL cut quartz crystal, a GT cut quartz crystal, an E cut quartz crystal, an MT cut quartz crystal, an ET cut quartz crystal, an FT cut quartz crystal, an NT cut quartz crystal, an H cut quartz crystal, a J cut quartz crystal, an RT cut quartz crystal, an SBTC cut quartz crystal, a TS cut quartz crystal, an X 30° cut quartz crystal, an LC cut quartz crystal, an AC cut quartz crystal, a BC cut quartz crystal, an NLSC cut quartz crystal, a Y cut quartz crystal, and an X cut quartz crystal.

3. The device of claim 1, wherein the first conductive film comprises one or more of gold, silver, titanium, platinum, copper, aluminum, and palladium.

4. The device of claim 1, wherein the first polymer coating is one or more of a polyacrylic, a polyester, a polyolefin, a polyvinyl, polycaprolactone, polystyrene, cycloolefin, polycarbonate, polyolefin, polypropylene, polymethylmethacrylate, polyvinyl alcohol, and polyethylene terephthalate.

5. The device of claim 1, wherein the first polymer coating has a thickness of about 0.4 nm to about 90 nm.

6. The device of claim 1, wherein the first polymer coating comprises about 0.4 fg/$\mu m^2$ to about 90 fg/$\mu m^2$ of a polymer material.

7. The device of claim 1, wherein the first polymer coating comprises a single layer of a polymer material.

8. The device of claim 1, wherein the first polymer coating comprises a plurality of layers of one or more polymer materials.

9. The device of claim 8, wherein the first polymer coating comprises about 2 polymer layers to about 10 polymer layers of the one or more polymer materials.

10. The device of claim 8, wherein the plurality of layers of the one or more polymer materials have a total thickness of about 0.8 nm to about 900 nm.

11. The device of claim 1, wherein the first polymer coating has a shape, the shape being one of a disk, a ring, a wheel, a quadrilateral, a triangle, a polygon, a pyramid, a cube, a cone, an ellipse, a cross, a grid, a cylinder, and a hemisphere.

12. The device of claim 1, wherein the second conductor is disposed on a second side of the oscillator crystal and wherein the first side of the oscillator crystal is opposite to the second side of the oscillator crystal.

13. A system to sense one or more odorants, the system comprising:

at least one device configured to sense the one or more odorants, the at least one device comprising:

an oscillator crystal having a first side and a second side;

a first conductive film in electrical communication with the first side of the oscillator crystal;

a second conductive film in electrical communication with the second side of the oscillator crystal;

a first conductor placed on the first side of the oscillator crystal and in electrical communication with the first conductive film;

a second conductor in electrical communication with the second conductive film;

a first polymer coating in physical communication with the first conductive film, wherein the first polymer coating has a first diffusivity constant for a first odorant, and a second diffusivity constant for a second odorant, and wherein the first diffusivity constant is greater than the second diffusivity constant; and a second polymer coating in physical communication with the second conductive film, wherein the second polymer coating has a different concentration than the first polymer coating;

an oscillator circuit having at least one first circuit input and at least one first circuit output, wherein the at least one first circuit input is in electrical communication with the first conductor, and wherein the at least one first circuit output is in electrical communication with the second conductor; and an electrical system in data communication with the oscillator circuit and configured to at least measure an oscillation frequency emitted by the oscillator crystal.

14. The system of claim 13, wherein the oscillator circuit is selected from the group consisting of a parallel resonant oscillator circuit, a series resonant oscillator circuit, a digital circuit, an analog circuit, a combination analog and digital circuit, a Pierce oscillator circuit, a Colpitts oscillator circuit, and a Clapp oscillator circuit.

15. The system of claim 13, further comprising an oscillator crystal housing configured to enclose the oscillator crystal, wherein the oscillator crystal housing comprises an electrically conductive material configured to effectively shield the oscillator crystal from a stray capacitance.

16. The system of claim 15, wherein the oscillator crystal housing further comprises an inside, an outside, and a plurality of voids configured to permit an odorant on the outside of the housing to enter the inside of the housing.

17. The system of claim 16, wherein the plurality of voids comprise holes in the oscillator crystal housing or an electrically conductive mesh.

18. The system of claim 13, wherein the at least one device comprises a plurality of devices to sense the one or more odorants.

19. The system of claim 13, wherein the second conductor is disposed on the second side of the oscillator crystal, and wherein the first side of the oscillator crystal is opposite to the second side of the oscillator crystal.

20. A method to sense one or more odorants, the method comprising:

providing a system to sense the one more odorants, the system comprising:

at least one device to sense the one or more odorants, the at least one device comprising:

an oscillator crystal having a first side and a second side;

a first conductive film in electrical communication with the first side of the oscillator crystal;

a second conductive film in electrical communication with the second side of the oscillator crystal;

a first conductor disposed on the first side of the oscillator crystal and in electrical communication with the first conductive film;

a second conductor in electrical communication with the second conductive film;

a first polymer coating in physical communication with the first conductive film; and a second polymer coating in physical communication with the second conductive film, wherein the first polymer coating has a different concentration than the second polymer coating, wherein the first polymer coating has a first diffusivity constant for a first odorant, and a second diffusivity constant for a second odorant, and wherein the first diffusivity constant is greater than the second diffusivity constant;

an oscillator circuit having at least a first circuit input and at least a first circuit output, wherein the at least first circuit input is in electrical communication with the first conductor, and wherein the at least first circuit output is in electrical communication with the second conductor; and an electrical system in data communication with the oscillator circuit and configured to at least measure an oscillation frequency emitted by the oscillator crystal;

exposing the system to some amount of an odorant;

measuring, using the electrical system, at least one oscillation frequency signal emitted by the oscillator crystal;

identifying, using the electrical system, the odorant based at least, in part, on the at least one oscillation frequency signal; and determining, using the electrical system, an amount of the odorant based at least, in part, on the at least one oscillation frequency signal.

21. The method of claim 20, wherein the odorant comprises one or more of a volatile organic compound, a solvent, a flavorant, a perfume, an amine, a thiol, a diamine, a triamine, acetone, trichloroethylene, phenylethyl alcohol, undecalactone, methanethiol, putrescine, cadaverine, butyric acid, butyric anhydride, indole, pyridine, skatole, trimethylamine, butyl seleno mercaptan, perchloroethylene, benzene, toluene, xylene, acetic acid, valeric acid, ethanol, butanol, and methanol.

22. The method of claim 20, wherein the measuring the at least one oscillation frequency signal comprises measuring at least one oscillation frequency signal emitted by the oscillator crystal over a period of time of about 10 seconds to about 300 seconds.

23. The method of claim 20, wherein the measuring the at least one oscillation frequency signal comprises:

measuring a first frequency emitted by the oscillator crystal in an absence of the odorant;

measuring a second frequency emitted by the oscillator crystal in the presence of the odorant; and calculating a difference between the first frequency and the second frequency.

24. The method of claim 20, wherein the measuring the at least one oscillation frequency signal comprises measuring an amplitude of the at least one oscillation frequency signal.

25. The method of claim 20, wherein the identifying the odorant comprises:

extracting, by the at least one device, at least one data component of the at least one oscillation frequency signal; and comparing, by the at least one device, the at least one data component to at least one data value of a look-up table having one or more data values associated with the one or more odorants or to at least one data value of a mathematical mode, wherein the at least one data component is one or more of an oscillator crystal frequency, a change in the oscillator crystal frequency, a rate of change in the oscillator crystal frequency, and an amplitude of the oscillator crystal frequency.

26. The method of claim 20, wherein the determining the amount of the odorant comprises:

extracting, by the at least one device, at least one data component of the at least one oscillation frequency signal; and comparing, by the at least one device, the at least one data component to at least one data value of a look-up table having one or more data values associated with the one or more odorants or to at least one data value of a mathematical mode, wherein the at least one data component is one or more of an oscillator crystal frequency, a change in the oscillator crystal frequency, a rate of change in the oscillator crystal frequency, and an amplitude of the oscillator crystal frequency.

27. The method of claim 20, wherein the second conductor is disposed on the second side of the oscillator crystal, and wherein the first side of the oscillator crystal is opposite to the second side of the oscillator crystal.

* * * * *